(12) United States Patent
Buchheister et al.

(10) Patent No.: US 8,500,276 B2
(45) Date of Patent: Aug. 6, 2013

(54) NON-REFLECTIVE IMAGING OPTICS FOR OPTICAL DEVICES, PARTICULARLY IN OPTHALMOLOGY

(75) Inventors: Jan Buchheister, Jena (DE); Lothar Müller, Ottendorf (DE); Marco Pretorius, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 175 days.

(21) Appl. No.: 13/024,668

(22) Filed: Feb. 10, 2011

(65) Prior Publication Data

US 2011/0199575 A1 Aug. 18, 2011

(30) Foreign Application Priority Data

Feb. 17, 2010 (DE) .......................... 10 2010 008 629

(51) Int. Cl.
*A61B 3/10* (2006.01)
*G02B 3/02* (2006.01)

(52) U.S. Cl.
USPC .......................................... 351/205; 359/720

(58) Field of Classification Search
USPC .................... 351/205, 207; 359/601, 708, 720
See application file for complete search history.

(56) References Cited

U.S. PATENT DOCUMENTS

| | | | |
|---|---|---|---|
| 3,985,422 A | 10/1976 | Mecklenborg et al. | |
| 4,415,239 A | 11/1983 | Humphrey | |
| 4,730,910 A | 3/1988 | Humphrey | |
| 4,838,680 A | 6/1989 | Nunokawa | |
| 6,585,374 B2 | 7/2003 | Matsumoto | |
| 7,810,929 B2 | 10/2010 | Mueller et al. | |
| 2010/0014052 A1 | 1/2010 | Koschmieder et al. | |

FOREIGN PATENT DOCUMENTS

| | | |
|---|---|---|
| DE | 35 19 442 A1 | 12/1985 |
| DE | 103 16 416 A1 | 10/2004 |
| DE | 10 2008 026 576 A1 | 12/2009 |
| DE | 10 2008 040 944 A1 | 2/2010 |
| WO | WO 2008/077526 A2 | 7/2008 |

*Primary Examiner* — Jack Dinh

(74) *Attorney, Agent, or Firm* — Patterson Thuente Pedersen, P.A.

(57) ABSTRACT

Imaging optics for optical devices, with which reflections of the illumination light, which is guided through the same optical elements as the observation light, are kept from reaching the observation pupil of the imaging beam path. The non-reflective imaging optics include at least two refractive optical elements, which are utilized for illumination as well as observation. The at least two refractive optical elements are designed approximately wedge-shaped and are tilted at a random azimuth angle of at least 5° and/or are positioned off-center in the beam path to block out the single reflections of the illumination, occurring at the optical system surfaces, for the observation. The imaging optics are for optical devices, particularly in ophthalmology thought the invention is applicable to other ophthalmological devices as well as to optical devices outside of this field.

8 Claims, 8 Drawing Sheets

(1 of 8 Drawing Sheet(s) Filed in Color)

NON-REFLECTIVE IMAGING OPTICS FOR OPTICAL DEVICES, PARTICULARLY IN OPTHALMOLOGY

This application claims priority to German Patent Application No. 102010008629.0 filed on Feb. 17, 2009, said application is incorporated herein by reference in its entirety.

BACKGROUND OF THE INVENTION

The invention is applicable particularly advantageously in cases in which the area to be observed, illuminated by the illumination, exhibits a very low reflectivity; as a result, the intensity, of the reflections of the illumination at optical boundary layers of the system, exceeds the utility light intensity or significantly interferes with the latter. Such systems include, for example, the ophthalmoscopic lens of a fundus camera used for the mapping of the eyeground since the degree of reflection of the fundus to be observed is very low.

According to known prior art, the basic design of a fundus camera exhibits a multilevel optical system. Thereby, an intermediate image of the retina is produced by an ophthalmoscopic lens, which is then mapped by an optical tracking system in an additional intermediate image and/or onto a film or photooptical array in the form of a CCD matrix. Thereby, the ophthalmoscopic lens is part of the illumination system as well as the imaging system.

A particular problem with fundus observation and imaging are the reflections at the cornea and the surfaces of the ophthalmoscopic lens since the intensity of the light, which is reflected by the retina and contains the actual image information of interest, is significantly lower than the intensity of the light, which is reflected before it enters the eye.

Disruptive cornea reflections are usually prevented through a separation of the pupil of the eye. Thereby, the ophthalmoscopic lens projects an illumination ring in the eye pupil, whereby the beams of the illumination, reflected on the cornea, miss the aperture of the observation system. Therefore, only the area within the illumination ring is used for observation. For the suppression of the reflections from the ophthalmoscopic lens, three concepts are essentially known, according to prior art.

DE 35 19 442 A1 describes an optical system in which light components which could enter the observation aperture through the reflection at the ophthalmoscopic lens or at the cornea are blocked out by means of black point plates. Thereto, the black point plates are arranged in a defined manner at a suitable location in the beam path and coated with light-absorbing layers. This type of reflection suppression has come to be known as "anti-reflection point."

A disadvantage of this concept is the proximity of the anti-reflection point to the field stop. The absorption of the individual light components can become visible as irregular illumination of the fundus. Ring-shaped shadows occur which impair the image impression and, therefore, impede the evaluation by the eye doctor.

Another solution is described in DE 103 16 416 A1. Thereby, the blocking of certain light components within the illumination optics is foregone. In place of the ophthalmoscopic lens, a multilens objective is provided, the lenses of which are tilted relative to one another in such a way that direct reflections at the optical boundary layers do not enter the aperture of the observation system.

Said solution requires significant expenditures for the mechanical mountings since a classical mounting of rotationally symmetric systems is not applicable. In order to keep the optical elements small, wedge-shaped lens segments develop which require a special mounting technology which has a negative impact on this second concept.

The use of lenses with only positive refractive power causes longitudinal chromatic aberrations and transverse chromatic aberrations which have to be elaborately compensated in the observation portion as well as the illumination portion of the downstream optical system. For applications with very small beam diameters, such as laser applications, the high number of optical boundary layers and the long glass path of the described objective also have a negative impact. Even slight contamination at the boundary layers and in the material can have adverse effects. As a result, the intensity greatly decreases and interfering stray light occurs.

The solution described in U.S. Pat. No. 4,730,910 A relates to an optical imaging system consisting of wide-angle lenses with stray light deflection, whereby illumination and imaging beam path are separated from one another. However, for the stray light deflection, the individual lenses are shifted so far that only one half of the lenses are utilized for the beam path.

This solution is disadvantageous in that several lenses are required for an effective correction of the resulting image defects and distortions. This significantly increases the expenditures regarding mounting and alignment.

Further focusing, particularly reflection-deflecting, spherical lens arrangements are described in U.S. Pat. No. 4,415,239 A. Thereto, the lens arrangements consist of a series of at least two optical elements with a cylindrical component each.

In order to block out the resulting reflections in said arrangements, it is necessary to significantly tilt the optical elements, which negatively impacts the image quality. Even though it is hereby also possible to reduce the extent of the tilting through a toric effect of the optical elements, the resulting higher-order aberrations, however, are unavoidable with this design. In addition, said approach to a solution also requires several lenses for an effective correction of the resulting image defects and distortions, significantly increasing the expenditures regarding mounting and alignment.

The third known concept, according to prior art, provides for the use of at least one mirror element instead of the ophthalmoscopic lens. Such systems exhibit simple mirror geometries, with which only a small observation field and/or illumination field can be realized with sufficient optical quality.

Other mirror systems, as described, e.g., in U.S. Pat. No. 6,585,374 B2, utilize movable parts in order to expand the small observation field and/or illumination field through scan movements. Thereto, elaborate mechanics for the precise movement and elaborate image processing techniques are required.

A further solution to said third concept is described in WO 2008/077526 A2. Through the use of mirror elements instead of the ophthalmoscopic lens, interfering reflections and chromatic aberrations of the optical media, caused by dispersion, can be avoided.

The optical system for ophthalmological devices and, particularly, fundus cameras, described in DE102008026576 A1, also relates to said third concept. With this solution it is possible to realize images of the eye fundus of very high quality, however, the manufacture of the at least two reflecting optical elements as well as mounting and alignment are elaborate and difficult.

FIELD OF THE INVENTION

The invention relates to imaging optics for optical devices with which, due to the design in accordance with the invention, reflections of the illumination light, which is guided through the same optical elements as the observation light, are kept from reaching the observation pupil of the imaging beam path.

SUMMARY OF THE INVENTION

Through the use of free-form geometries, it is possible to achieve a great working distance and a large field of view with good optical quality. However, for the suggested basic design, the great working distance has a negative effect on the frame size of the mirror elements. Through the use of free-form surfaces on reflective elements, the manufacture of the elements is very elaborate due to the high tolerance sensitivity. The same applies to the alignment of said elements.

Based on the disadvantages of the known solutions, according to prior art, the invention is based on developing non-reflective imaging optics for optical devices, which avoid stray light through single reflections at optical boundary layers in principle, realize a large observation and illumination field, utilize compact and light components without elaborate mechanics and/or software, and which can thereby be manufactured and aligned significantly more cost-effectively.

Through non-reflective imaging optics for optical devices, particularly in ophthalmology, comprising at least two refractive optical elements, which are utilized for illumination as well as observation, said task is solved in such a way that the at least two refractive optical elements are designed approximately wedge-shaped and are tilted at a random azimuth angle of at least 5° and/or are positioned off-center in the beam path in order to block out the single reflections of the illumination occurring at the optical system surfaces for the observation.

The non-reflective imaging optics, according to the invention, are provided for optical devices, particularly in ophthalmology. Even though the presented embodiment examples for the observation and/or documentation of the eye fundus have been optimized, the disclosed operating principle in this patent application for correcting and/or minimizing of occurring image defects and/or distortions through the use of refractive optical elements with optical system surfaces in the form of free-form surfaces is also applicable to other ophthalmological devices and, of course, to optical devices outside of the field of ophthalmology.

BRIEF DESCRIPTION OF THE DRAWINGS

The patent or application file contains at least one drawing executed in color. Copies of this patent with color drawing(s) will be provided by the Patent and Trademark Office upon request and payment of the necessary fee.

In the following, the invention is further described by means of embodiment examples. Thereto, it is shown in.

DETAILED DESCRIPTION

According to the invention, the non-reflective imaging optics for optical devices, particularly in ophthalmology, consist of at least two refractive optical elements, which are utilized for illumination as well as observation. Thereby, the at least two refractive optical elements are designed approximately wedge-shaped and are tilted at a random azimuth angle of at least 5° and/or are positioned off-center in the beam path in order to block out the single reflections of the illumination, occurring at the optical system surfaces, for the observation.

Tilting the refractive optical elements and/or their system surfaces refers to the tilting of optically active surfaces with regard to the reference axis in at least one azimuth. The reference axis is identical with the beam which runs through the center of the field stop and aperture diaphragm. Through tilting of a surface, the reference axis and the face normal form a nonzero degree angle at the intersection point of the reference axis. According to the invention, the amount of tilt of at least one system surface of a refractive optical element is defined in a random azimuth>5°. The tilting of a refractive optical element is effected through the like-minded tilting of its optically active system surfaces.

Analogous to the definition of tilting, the approximately wedge-shaped design of the refractive optical elements is, according to the invention, defined in such a way that both optical functional surfaces of a refractive optical element are tilted to one another in the same azimuth at an angle>5°.

Figure 1:
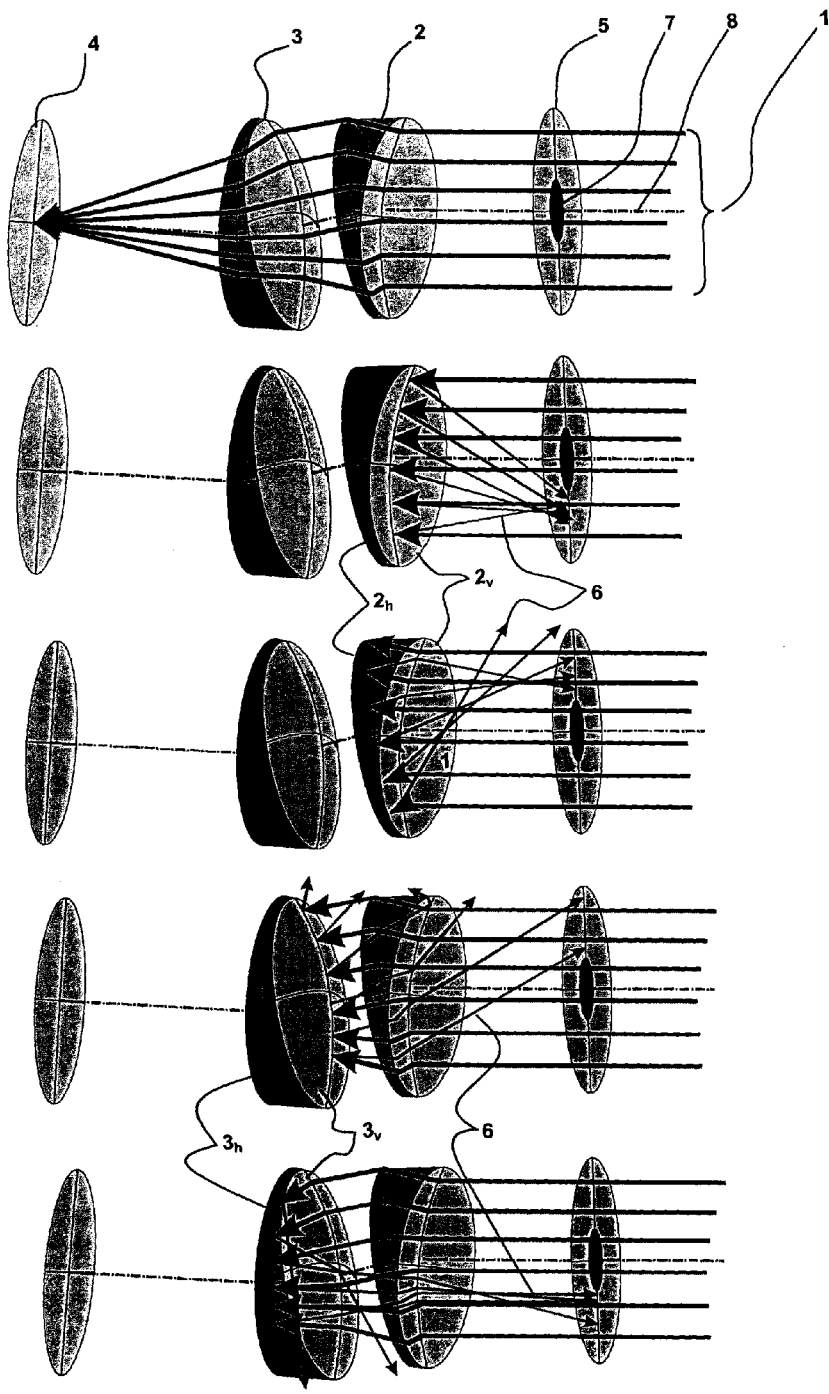
FIG. 1 is a schematic diagram of the illumination beam path of non-reflective imaging optics with the single reflections occurring at the individual system surfaces.

In order to illustrate the principle of operation, according to the invention, of the non-reflective imaging optics for optical devices, particularly in ophthalmology, FIG. 1 shows a schematic diagram of the illumination beam path of non-reflective imaging optics with the single reflections occurring at the individual system surfaces.

According to the first partial representation, the illumination beams 1, originating from the illumination source (not shown), are focused via two refractive optical elements 2 and 3 in the object plane 4. The light reflected in the object plane is mapped with the image information again via the two refractive optical elements 2 and 3 in the object plane 5, which represents the coupling point between illumination and observation beam path. Thereby, single reflections 6 of the illumination beams 1 are to be blocked out for the observation at the optical system surfaces $2_v$ and $2_h$ as well as $3_v$ and $3_h$, i.e., not impinge on the area of interest 7. Thereto, the two refractive optical elements 2 and 3 are designed approximately wedge-shaped and are tilted at a random azimuth angle of at least 5° and/or are positioned off-center in the beam path, which is defined by the reference axis 8. Thereby, the area of interest 7 does not necessarily have to coincide with the plane 5, which represents the coupling point between illumination and observation beam path.

The second partial representation of FIG. 1 shows that the single reflections 6 of the illumination beams 1, occurring at the anterior optical system surfaces $2_v$ of the refractive optical element 2 are blocked out and do not impinge on the area of interest 7.

The additional partial representations of FIG. 1 show that the single reflections 6 of the illumination beams 1, occurring at the posterior optical system surfaces $2_h$ of the refractive optical element 2 as well as at the anterior 3, and posterior system surfaces $3_h$ of the refractive optical element 3 are also blocked out and do not impinge on the area of interest 7.

In a particularly advantageous embodiment, at least two of the optical system surfaces of the at least two approximately wedge-shaped refractive optical elements, tilted in the beam path, are designed as free-form surfaces, while the remaining system surfaces of the at least two approximately wedge-shaped refractive optical elements, tilted in the beam path, exhibit an aspherical, toric, or even spherical shape.

The at least two refractive optical elements are arranged to one another in such a way that the occurring spots are minimized with regard to their expansion. The position of the focal points of the spots defines the position of the pixels. The positional deviation of said pixels with regard to the position calculated from the coordinates of the object plane with a fixed image ratio is called distortion.

In the known systems for fundus imaging, according to prior art, distortion values of less than 2% are achieved for a field diameter up to an angle of field at the eye of 30°. However, for the entire field of view up to an angle of field of 50°, only values between 5% and 10% are generally realized.

By contrast, through the use of free-form surfaces, distortion values around 1% for an angle of field of up to 30° and around 2% for the entire angle of field can be achieved with the solution, according to the invention.

Due to the break of the symmetry of the overall system of the non-reflective imaging optics, at least two of the optical system surfaces of the at least two approximately wedge-shaped refractive optical elements, tilted in the beam path, according to the invention are designed as free-form surfaces. Only then is it possible to correct occurring image defects and/or distortions with a minimum number of (two) refractive optical elements in such a way that with a downstream positioned rotationally symmetrical imaging system, a sufficiently high image quality for the application is achieved.

In a further example embodiment, the optical system surfaces, designed as free-form surfaces, of the at least two approximately wedge-shaped refractive optical elements, tilted in the beam path, exhibit toric effects, i.e., the contributing refractive power of the optical system surface is different from the contributing refractive power in the azimuth of 90° thereto.

As a result, the tilt angles of basically convex system surfaces and the approximate wedge shapes of the refractive optical elements can be decreased.

Other occurring unsymmetrical image defects are reduced through the decreased tilt angles of the system surfaces and the interrelated decreased wedge shapes of the refractive optical elements.

The toric effect of the free-form surface on an optical system surface has the advantage that its tilt angle can be reduced when the tilting and/or decentering of the system surface in the azimuth is effected with the lower refractive power, possibly even with a negative refractive power. As a result, the occurring single reflections diverge less strongly in said azimuth, and non-reflectivity can nonetheless be ensured.

The greater refractive power in the other azimuth contributes to the overall refractive power of the imaging optics. Hereby, a separation of the refractive powers onto several system surfaces can be effected, which in turn is favorable with regard to the decrease in image defects.

Advantageously, the compensation of the astigmatic effect, caused by the break with the symmetry of the overall system, takes place on a surface less critical for the non-reflectivity.

Said effect is particularly effective at the anterior optical system surface 2, of the refractive optical element 2 (see FIG. 1) since the single reflections, produced by the convex surface shape, exhibit a great divergence. There are no other refractive optical elements, which can contribute to the decrease of said divergence. Therefore, the reflection on the plane 5 becomes very large and can only be blocked out from the observation, particularly the area of interest 7, through a very severe tilting of said anterior optical system surface $2_v$.

The free-form surfaces on the optical system surfaces are described with X-Y polynomials. The center of the surfaces is de-centered in such a way that the main beam of the axis bundle of the observation beam path runs approximately through the surface center. The original position of the polynomial expansion is enabled as an optimization variable. As a result, a redundancy of the variables during optimization is avoided, and the polynomial expansion can take place at the optimal spot.

Of course, system surfaces can also be defined and optimized with alternative methods, such as Zernike expansions or Spline descriptions.

For the following embodiment examples, which are optimized particularly for a fundus camera, all components are positioned in such a way that 30 to 60 mm of open working distance remains between the eye of the subject and the non-reflective imaging optics. As a result, the ergonomic aspects with regard to the patient are fulfilled as well as sufficient manipulative freedom being provided for the physician during the examination of the patient's eye.

In a first embodiment example, the non-reflective imaging optics consist of two refractive optical elements, whereby the anterior system surfaces of both refractive optical elements are designed as free-form surfaces, the posterior system surface of the first refractive optical element is designed as torus, and the posterior system surface of the second refractive optical element is designed as a sphere, and the overall design of which can be described as follows:

| Surface | Radius [mm] | Thickness [mm] | Glass | Comment |
|---|---|---|---|---|
| SA = BQ | 0.000000 | 127.023559 | | |
| ZB | 0.000000 | 33.434954 | | |
| $2_v$ | 460.241355 | 40.000000 | N-LAK8 | XY polynomial |
| $2_h$ | −112.724233 | 3.416369 | | Torus |
| $3_v$ | 67.330573 | 21.208847 | N-LAK8 | Sphere |
| $3_h$ | −553.072593 | 49.259906 | | XY polynomial |
| P = IA | 0.000000 | 17.000000Y | Ideal lens | f' = 17 mm |
| R | 0.000000 | | | |

Position of the surfaces:

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

Translation of the coordinate systems:

| Surface | X [mm] | Y [mm] | Z [mm] |
|---|---|---|---|
| $2_v$ | −0.015804 | −0.009449 | 0.000000 |
| $2_h$ | −0.176313 | 4.129852 | 0.000000 |
| $3_v$ | −1.160058 | 9.969841 | 0.000000 |
| $3_h$ | 0.397186 | 4.114025 | 0.000000 |
| P = IA | 0.194216 | 2.831227 | 0.000000 |

Rotation of the coordinate systems with regard to eye pupil (in air):

| Surface | Alpha [degree] | Beta [degree] | Gamma [degree] |
|---|---|---|---|
| $2_v$ | −9.715970 | −0.842779 | 0.000000 |
| $2_h$ | −14.376718 | 16.307588 | 0.000000 |
| $3_v$ | −9.946335 | 15.458494 | 0.000000 |
| $3_h$ | −11.913235 | 2.391050 | 0.000000 |
| P = IA | 1.482621 | −0.261571 | −0.138182 |

Description of the surface shapes of surfaces $2_v$, $2_h$, $3_h$:
Surface 2v:

| | | | |
|---|---|---|---|
| $K_x =$ | 0.000000000E+00 | $K_y =$ | 0.000000000E+00 |
| $1/\rho_x =$ | 262.029626 | $1/\rho_y =$ | 460.241355 |
| $c_{1-3}$ | −8.16682913E−02 | 1.30744652E−02 | 3.41935416E−03 |
| $c_{4-6}$ | −7.06926443E−04 | 2.79954523E−03 | −7.24668714E−05 |
| $c_{7-9}$ | −7.13866226E−05 | −8.22329726E−05 | −7.79315372E−05 |
| $c_{10-12}$ | −3.21596886E−07 | 1.76630879E−07 | −5.03015616E−07 |
| $c_{13-15}$ | −2.78639559E−07 | −1.02664121E−06 | 8.17043798E−09 |
| $c_{16-18}$ | 1.47741005E−08 | 2.45319524E−08 | −6.39279788E−09 |
| $c_{19-21}$ | 7.16686190E−09 | −2.93771547E−09 | 2.40054911E−11 |
| $c_{22-24}$ | 3.80865136E−12 | 3.12139213E−10 | −2.66011419E−10 |
| $c_{25-27}$ | −2.10800584E−10 | 8.11033757E−11 | 1.06969528E−11 |

Surface $2_h$:

| | | | |
|---|---|---|---|
| $K_x =$ | 0.000000000E+00 | $K_y =$ | 0.000000000E+00 |
| $1/\rho_x =$ | −192.389983 | $1/\rho_y =$ | −112.724233 |
| $c_{1-27}$ | 0.000000000E−00 | | |

Surface $3_h$:

| | | | |
|---|---|---|---|
| $K_x =$ | 0.000000000E+00 | $K_y =$ | 0.000000000E+00 |
| $1/\rho_x =$ | −626.781667 | $1/\rho_y =$ | −553.072593 |
| $c_{1-3}$ | 1.46571567E−02 | −4.19559905E−02 | 2.47038454E−03 |
| $c_{4-6}$ | 1.30391601E−03 | 4.05033404E−03 | −1.10654287E−04 |
| $c_{7-9}$ | −1.18192140E−04 | −1.08606641E−04 | −1.01909142E−04 |
| $c_{10-12}$ | −9.70012347E−07 | 5.68458154E−07 | 3.06807937E−06 |
| $c_{13-15}$ | −1.85585147E−07 | 5.49978310E−07 | 1.31161920E−08 |
| $c_{16-18}$ | 2.50938306E−08 | 2.12181386E−08 | −4.80230112E−08 |
| $c_{19-21}$ | −4.51844849E−09 | −1.37209572E−08 | −2.41037488E−10 |
| $c_{22-24}$ | −9.94991837E−11 | −1.48481266E−09 | 3.35571849E−10 |
| $c_{25-27}$ | 5.06355656E−10 | 7.62147783E−10 | 3.68207235E−10 |

Figure 2A:
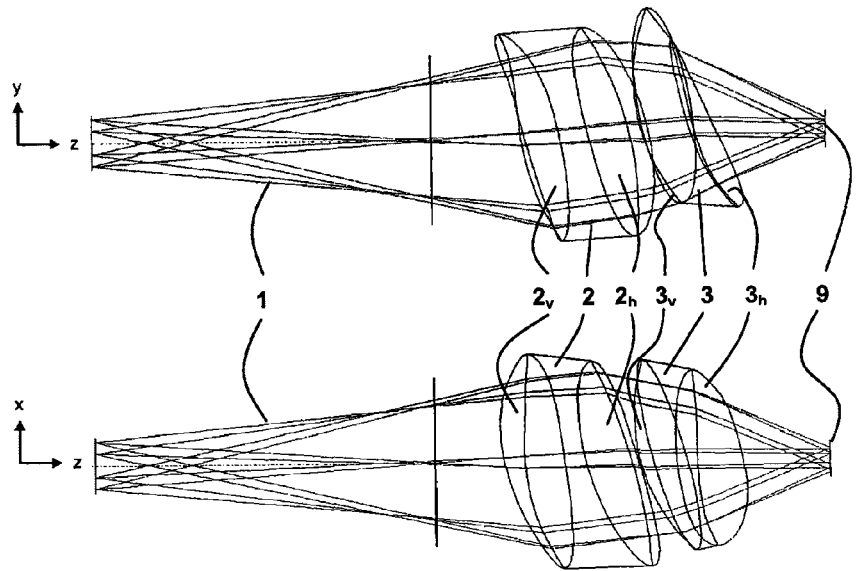
FIG. 2a depicts the illumination beam path of a first imaging optics system, according to the invention, with two refractive optical elements, the system surfaces of which are designed in the form of two free-form surfaces, a torus, and a sphere.

Thereto, FIG. 2a shows the (idealized) illumination beam path of the first imaging optics, according to the invention, with two refractive optical elements, the system surfaces of which are designed in the form of two free-form surfaces, a torus, and a sphere.

The illumination beams 1 in the form of an annular illumination are focused in the eye pupil plane 9, starting from the (not depicted) illumination source via two refractive optical elements 2 and 3. Thereby, the two refractive, approximately wedge-shaped optical elements 2 and 3 are tilted at a random azimuth angle of at least 5° and/or positioned off-center in the beam path. Single reflections (not depicted) of the illumination beams 1, which occur at the optical system surfaces $2_v$ and $2_h$ as well as $3_v$ and $3_h$, are to be blocked out for the observation. For said purpose, the anterior system surfaces $2_v$ and $3_v$ of both refractive optical elements 2 and 3 are designed as free-form surfaces, the posterior system surface $2_h$ of the first refractive optical element 2 is designed as a torus, and the posterior system surface $3_h$ of the second refractive optical element 3 is designed as a sphere.

Figure 2B:
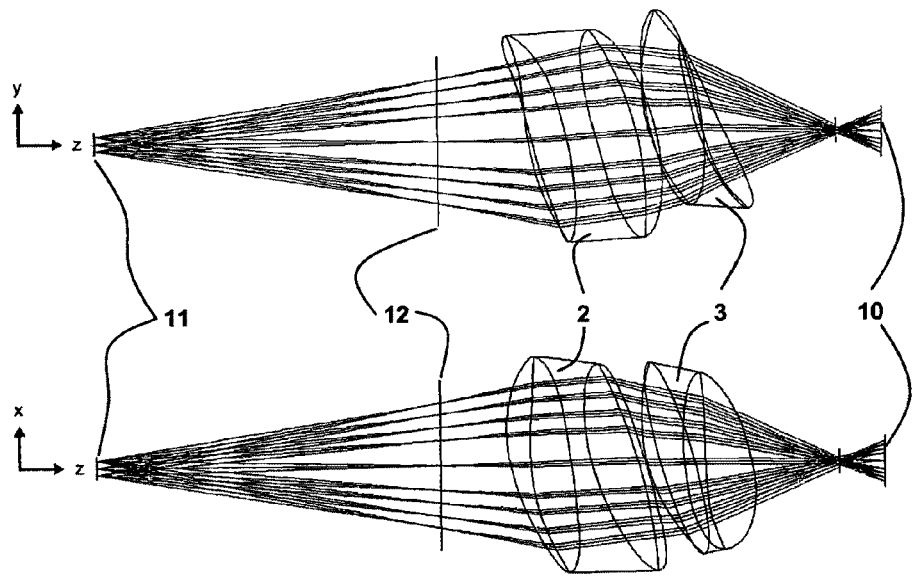
FIG. 2b depicts the observation beam path of a first imaging optics system, according to the invention, with two refractive optical elements, the system surfaces of which are designed in the form of two free-form surfaces, a torus, and a sphere.
Figure 2C:
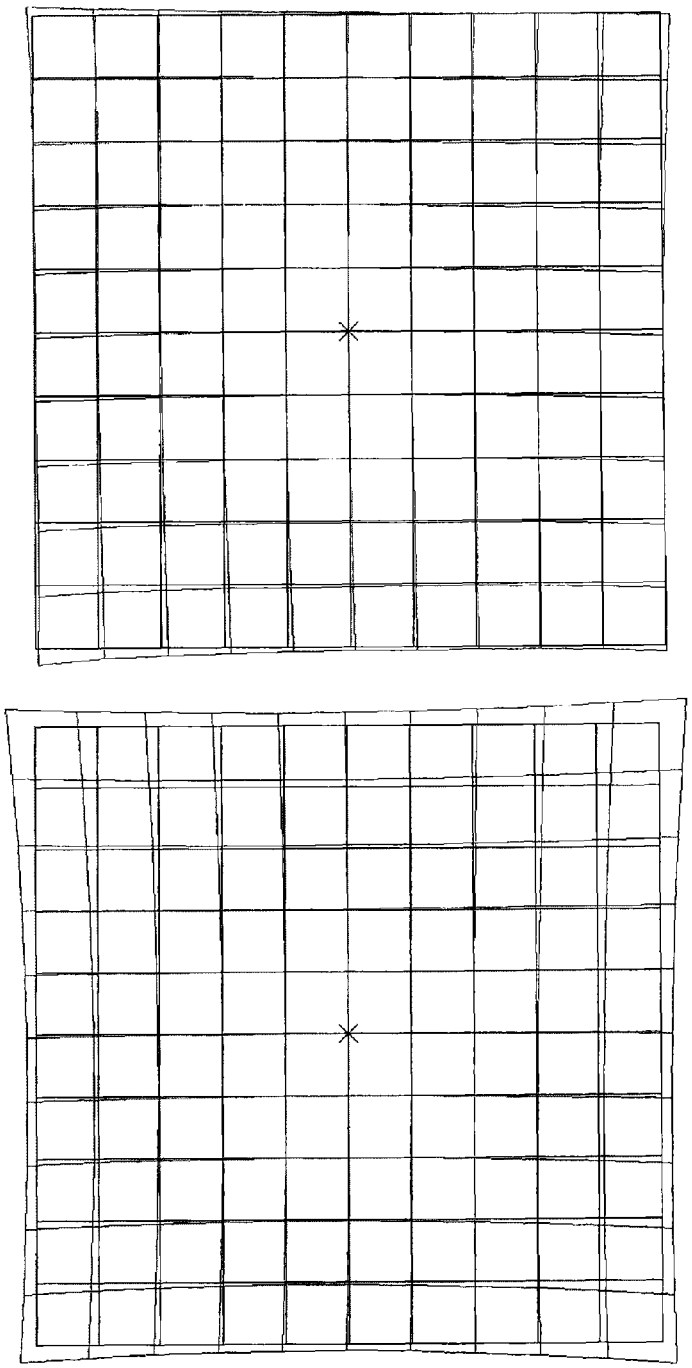
FIG. 2c depicts the thereby occurring distortion grid related to FIGS. 2a and 2b of the imaging optics on the retina juxtaposed to imaging optics known from prior art.

FIG. 2b shows the respective observation beam path of the second imaging optics, according to the invention, with two refractive optical elements, whereby the anterior system surfaces of both refractive optical elements are designed as free-form surfaces, the posterior system surface of the first refractive optical element is designed as torus, and the posterior system surface of the second refractive optical element is designed as a sphere, and an eye idealized through a substitute focal length.

The image of the retina 10 is mapped in the aperture diaphragm 11 via the two refractive optical elements 2 and 3, whereby an intermediate image of the retina is produced in the plane 12. Through the optical system surfaces $2_v$ and $2_h$ as well as $3_v$ and $3_h$, designed in accordance with the invention, occurring single reflections (not depicted) of the illumination beams are blocked out for the observation, therefore not impinging on the aperture diaphragm 11.

Figure 3A:
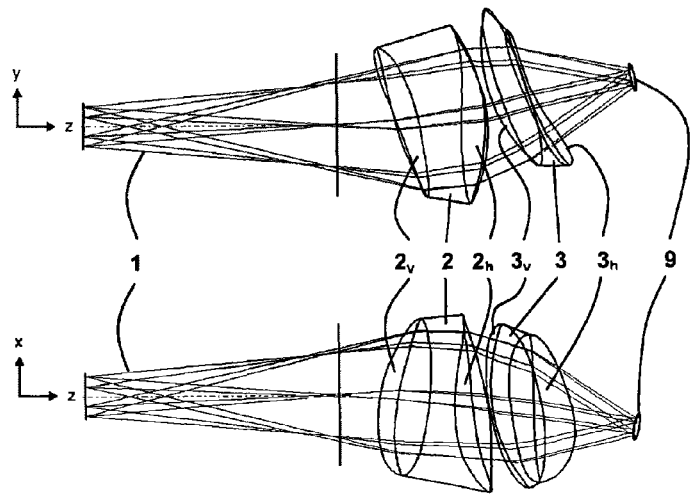
FIG. 3a depicts the illumination beam path of a second imaging optics system, according to the invention, with two refractive optical elements, the system surfaces of which are designed in the form of three free-form surfaces, and an asphere.
Figure 3B:
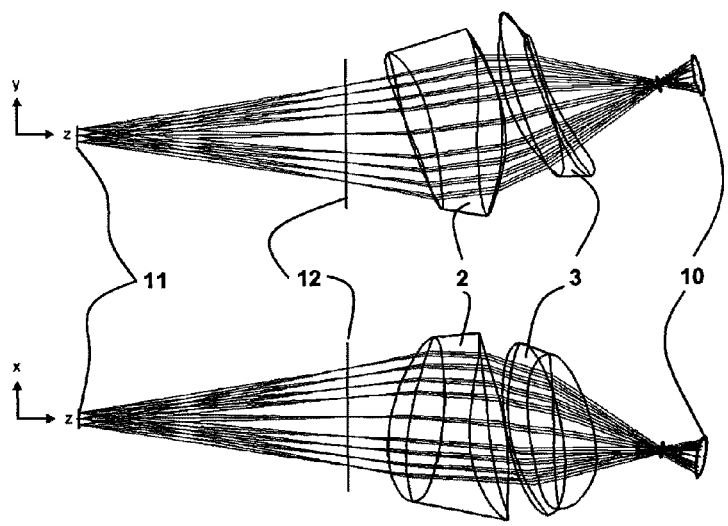
FIG. 3b depicts the observation beam path of a second imaging optics system, according to the invention, with two refractive optical elements, the system surfaces of which are designed in the form of three free-form surfaces, and an asphere.
Figure 3C:
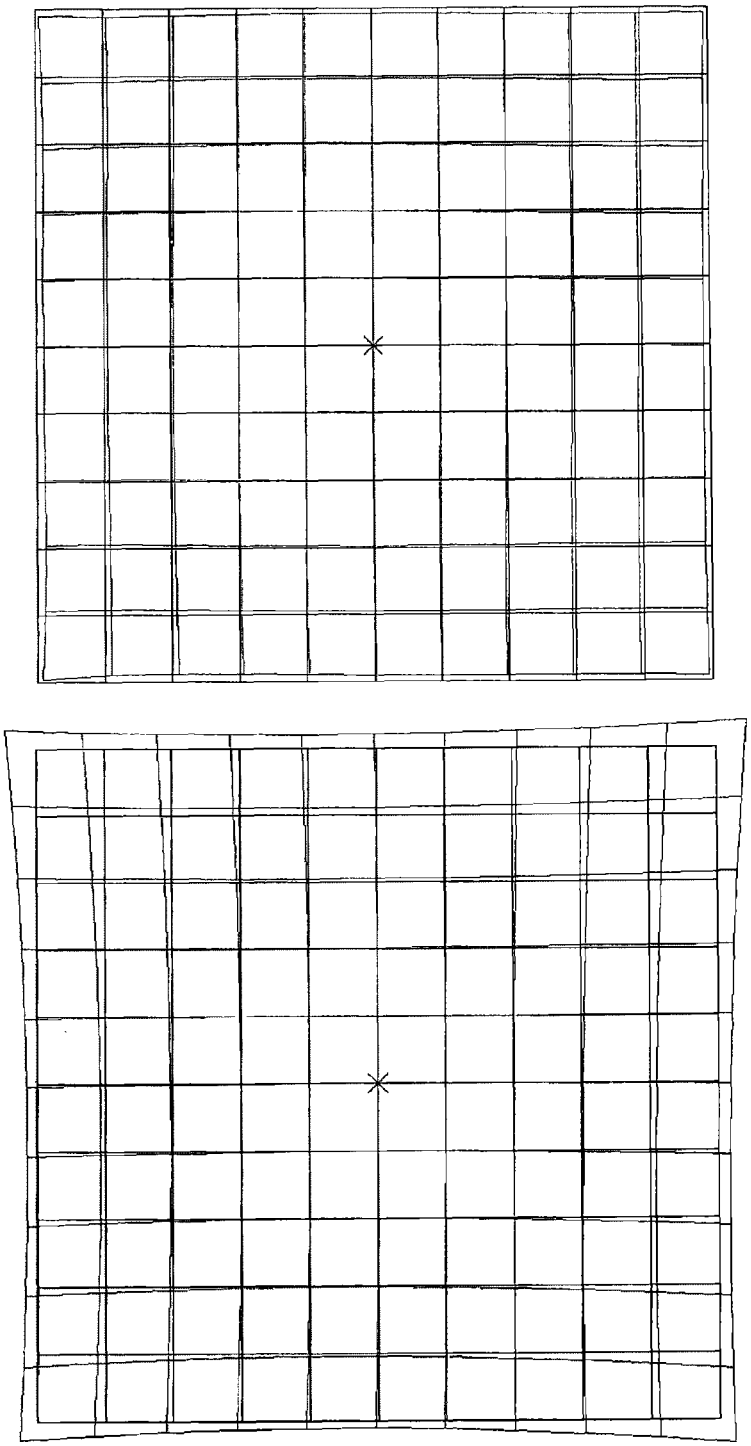
FIG. 3c depicts the thereby occurring distortion grid related to FIGS. 3a and 3b of the imaging optics on the retina juxtaposed to imaging optics known from prior art.

Thereto, FIG. 3c shows for this solution the occurring distortion grid of the imaging optics on the retina juxtaposed to the distortion grid of imaging optics known from prior art, according to DE 103 16 416 A1. It can be seen that compared to the solution from prior art, the distortions are diminished.

Hereby, the posterior system surface $3_h$ of the second refractive optical element 3 is designed as torus, i.e., the system surface $3_h$ exhibits two different radii in two azimuth angles, rotated against each other at 90°. A rotation of the system surface $3_h$ around the optical axis could result in an even more favorable impact on the image defects.

This first embodiment example confirms that non-reflective imaging optics comprising only two refractive optical elements can be realized if thereby at least two of the system surfaces are designed as free-form surfaces; hereby, however, compromises still have to be made with regard to image quality.

In a second embodiment example, the non-reflective imaging optics comprise two refractive optical elements, whereby the anterior and posterior system surface of the first refractive optical element, and the posterior system surface of the second refractive optical element are designed as free-form surfaces, and the anterior system surface of the second refractive optical element is designed as an asphere. Hereby, the rotationally symmetrical asphere is used off-axis. The overall design can be described as follows:

| Surface | Radius [mm] | Thickness [mm] | Glass | Comment |
|---|---|---|---|---|
| SA = BQ | 0.000000 | 112.723657 | | |
| ZB | 0.000000 | 26.315884 | | |
| $2_v$ | 460.241355 | 40.000000 | N-LAK8 | XY polynomial |
| $2_h$ | −98.378083 | 2.432516 | | XY polynomial |
| $3_v$ | 69.369038 | 18.428907 | N-LAK8 | Asphere |
| $3_h$ | −553.072593 | 45.324601 | | XY polynomial |
| P = IA | 0.000000 | 17.000000Y | Ideal lens | f' = 17 mm |
| R | 0.000000 | | | |

Position of the surfaces:
Translation of the coordinate systems:

| Surface | X [mm] | Y [mm] | Z [mm] |
|---|---|---|---|

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

| Surface | X [mm] | Y [mm] | Z [mm] |
|---|---|---|---|
| $2_v$ | −0.008249 | −0.004878 | 0.000000 |
| $2_h$ | −3.632256 | 4.940808 | 0.000000 |
| $3_v$ | −7.513007 | 12.906752 | 0.000000 |
| $3_h$ | −6.767967 | 10.354774 | 0.000000 |
| P = IA | −15.095604 | 20.046330 | 0.000000 |

Rotation of the coordinate systems with regard to eye pupil (in air):

| Surface | Alpha [degree] | Beta [degree] | Gamma [degree] |
|---|---|---|---|
| $2_v$ | −16.627633 | −12.552204 | 0.000000 |
| $2_h$ | −2.975360 | 9.652402 | 0.000000 |
| $3_v$ | −18.533878 | 9.595629 | 0.000000 |
| $3_h$ | −17.902422 | 1.472894 | 0.000000 |
| P = IA | −12.055657 | −10.186383 | −1.343352 |

-continued

Description of the surface shapes of surfaces $2_v$, $2_h$, $3_h$:
Surface $2_v$:

| | | | | |
|---|---|---|---|---|
| $K_x =$ | 0.000000000E+00 | $K_y =$ | | 0.000000000E+00 |
| $1/\rho_x =$ | 262.029626 | $1/\rho_y =$ | | 460.241355 |
| $c_{1-3}$ | −1.076219235E−02 | −1.939046941E−03 | | 1.997905625E−03 |
| $c_{4-6}$ | 1.746907059E−03 | 2.461118134E−03 | | −6.571983437E−05 |
| $c_{7-9}$ | −9.883077652E−06 | −5.445029935E−05 | | −1.632332880E−05 |
| $c_{10-12}$ | −3.984223970E−07 | 6.025247976E−07 | | −3.447675743E−07 |
| $c_{13-15}$ | 6.588778570E−08 | −9.912377449E−07 | | 6.020462360E−09 |
| $c_{16-18}$ | −1.953270172E−10 | 7.786357428E−09 | | −1.948376196E−09 |
| $c_{19-21}$ | 7.040827309E−09 | −8.579730212E−09 | | 1.890823354E−10 |
| $c_{22-24}$ | 1.545069767E−11 | −3.939617920E−11 | | −1.872836301E−10 |
| $c_{25-27}$ | −1.433811680E−10 | −3.180424756E−10 | | 5.075901345E−11 |

Surface $2_h$:

| | | | | |
|---|---|---|---|---|
| $K_x =$ | 0.000000000E+00 | $K_y =$ | | 0.000000000E+00 |
| $1/\rho_x =$ | −100.942861 | $1/\rho_y =$ | | −98.378083 |
| $c_{1-3}$ | 5.282970718E−03 | −2.390734163E−02 | | 9.280180593E−04 |
| $c_{4-6}$ | 7.885552729E−04 | −1.715965007E−03 | | 2.046197629E−05 |
| $c_{7-9}$ | 1.927024556E−05 | 8.531615103E−05 | | −1.605061381E−05 |
| $c_{10-12}$ | 5.617458102E−07 | 3.689124959E−07 | | 7.443694101E−07 |
| $c_{13-15}$ | −5.994160512E−07 | 2.282951119E−07 | | −5.812076272E−09 |

$$z = \frac{\rho h^2}{1 + \sqrt{1 - (1+\kappa)\rho^2 h^2}} + \sum_{k=1} c_k h^{2k+2}$$

| | | | | |
|---|---|---|---|---|
| $c_{16-18}$ | −1.723649589E−09 | −8.769239055E−09 | | −9.773820261E−10 |
| $c_{19-21}$ | −4.698271820E−09 | −1.704652063E−08 | | 1.317751719E−10 |
| $c_{22-24}$ | 2.089880410E−10 | 3.761425386E−10 | | 1.878879381E−11 |
| $c_{25-27}$ | −7.245340147E−11 | −9.975912395E−11 | | −9.207989014E−11 |

Surface $3_h$:

| | | | | |
|---|---|---|---|---|
| $K_x =$ | 0.000000000E+00 | $K_y =$ | | 0.000000000E+00 |
| $1/\rho_x =$ | −626.781667 | $1/\rho_y =$ | | −553.072593 |
| $c_{1-3}$ | 2.487303401E−02 | −6.337149712E−02 | | 5.842772050E−04 |
| $c_{4-6}$ | 3.650951912E−04 | 3.800070084E−03 | | −6.340939346E−05 |
| $c_{7-9}$ | −4.948991848E−05 | −1.560159975E−04 | | −2.586127402E−05 |
| $c_{10-12}$ | 9.681634924E−07 | 9.072631039E−07 | | 1.675755763E−06 |
| $c_{13-15}$ | 9.789720502E−07 | 5.079850594E−07 | | 9.057671419E−09 |
| $c_{16-18}$ | −5.038663621E−09 | −6.726531096E−10 | | −2.375679687E−08 |
| $c_{19-21}$ | −3.868956663E−09 | −1.420798036E−08 | | −4.135849189E−10 |
| $c_{22-24}$ | −7.758610476E−11 | −1.701714743E−09 | | −1.760333486E−11 |
| $c_{25-27}$ | −5.742161539E−10 | −1.914559861E−11 | | −3.980153064E−10 |

Description of the surface shape of surface $3_v$:

| | | | |
|---|---|---|---|
| $K =$ | 8.835330521E−02 | | |
| $1/\rho =$ | 69.369038 | | |
| $c_{1-3}$ | 0.000000000E−00 | 0.000000000E−00 | 0.000000000E−00 |

Thereto, FIG. 3a shows the (idealized) illumination beam path of the second imaging optics, according to the invention, with two refractive optical elements, the system surfaces of which are designed in the form of three free-form surfaces, and an asphere.

Hereby, the illumination beams 1 in the form of an annular illumination are also focused in the eye pupil plane 9, starting from the (not depicted) illumination source via two refractive optical elements 2 and 3. Single reflections (not depicted) of the illumination beams 1, which occur at the optical system surfaces $2_v$ and $2_h$ as well as $3_v$ and $3_h$, are also to be blocked out for the observation. For said purpose, the system surfaces of the two refractive, approximately wedge-shaped optical elements 2 and 3, tilted at a random azimuth angle of at least 5° and/or positioned off-center in the beam path, are designed as free-form surfaces, with the exception of the anterior system surface $3_v$ of the second refractive optical element $3_v$ which is designed as an asphere.

FIG. 3b shows the respective observation beam path of the second imaging optics, according to the invention, with two refractive optical elements, the system surfaces of which are designed in the form of three free-form surfaces, and an asphere, and an eye idealized through a substitute focal length.

The image of the retina 10 is mapped in the aperture diaphragm 11 via the two refractive optical elements 2 and 3, whereby an intermediate image of the retina is produced in the plane 12. Through the optical system surfaces $2_v$ and $2_h$ as well as $3_v$ and $3_h$, designed in accordance with the invention, occurring single reflections (not depicted) of the illumination beams are blocked out for the observation, therefore not impinging on the aperture diaphragm 11.

Contrary to the solutions in prior art, the distortion values achieved with this solution are around 1% for an angle of field of up to 30° and around 2% for the entire angle of field.

Thereto, FIG. 3c shows for this solution the occurring distortion grid of the imaging optics on the retina juxtaposed to the distortion grid of imaging optics known from prior art, according to DE 103 16 416 A1.

The herein suggested and described embodiment example is characterized by the non-reflection in the area of interest, very little distortion, a wide open working distance, and only two refractive optical elements, which are comparatively small and manufactured cost-effectively.

In a third embodiment example, the non-reflective imaging optics comprise two refractive optical elements, whereby the anterior and posterior system surface of the first refractive optical element, and the posterior system surface of the second refractive optical element are designed as a free-form surface, and the anterior system surface of the second refractive optical element is designed as a sphere. The overall design can be described as follows:

| Surface | Radius [mm] | Thickness [mm] | Glass | Comment |
|---|---|---|---|---|
| SA = BQ | 0.000000 | 123.394223 | | |
| ZB | 0.000000 | 36.178305 | | |
| $2_v$ | 460.241355 | 39.210908 | N-LAK8 | XY polynomial |
| $2_h$ | −98.378083 | 2.041868 | | XY polynomial |
| $3_v$ | 69.665916 | 17.941242 | N-LAK8 | |
| $3_h$ | −553.072593 | 50.945958 | | XY polynomial |
| P = IA | 0.000000 | 17.000000Y | Ideal lens | f' = 17 mm |
| R | 0.000000 | | | |

Position of the surfaces:
Translation of the coordinate systems:

| Surface | X [mm] | Y [mm] | Z [mm] |
|---|---|---|---|
| $2_v$ | −0.011617 | −0.016130 | 0.000000 |
| $2_h$ | 0.974295 | 3.470584 | 0.000000 |
| $3_v$ | −3.363366 | 10.952433 | 0.000000 |
| $3_h$ | 0.658348 | 5.474388 | 0.000000 |
| P = IA | −0.182751 | 9.037957 | 0.000000 |

Rotation of the coordinate systems with regard to eye pupil (in air):

| Surface | Alpha [degree] | Beta [degree] | Gamma [degree] |
|---|---|---|---|
| $2_v$ | −11.950087 | −1.103246 | 0.000000 |
| $2_h$ | −7.561127 | 12.292050 | 0.000000 |
| $3_v$ | −10.640443 | 13.236519 | 0.000000 |

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

| | | | |
|---|---|---|---|
| $3_h$ | −9.340704 | 1.838853 | 0.000000 |
| P = IA | −3.992984 | −0.936974 | 0.033760 |

Description of the surface shapes of surfaces $2_v$, $2_h$, $3_h$:
Surface $2_v$:

| | | | |
|---|---|---|---|
| $K_x$ = | 0.000000000E+00 | $K_y$ = | 0.000000000E+00 |
| $1/\rho_x$ = | 262.029626 | $1/\rho_y$ = | 460.241355 |
| $c_{1-3}$ | −7.816294472E−02 | −6.769775549E−04 | 3.512000519E−03 |
| $c_{4-6}$ | −1.933397623E−04 | 3.323904852E−03 | −7.073432239E−05 |
| $c_{7-9}$ | −5.175690025E−05 | −4.246655458E−05 | −5.977805266E−05 |
| $c_{10-12}$ | 1.661105408E−07 | 2.387423681E−07 | −2.140049981E−07 |
| $c_{13-15}$ | −2.624390743E−07 | −1.155402838E−06 | 5.256645482E−09 |
| $c_{16-18}$ | 1.507180023E−08 | 2.590824277E−08 | −9.019395714E−09 |
| $c_{19-21}$ | 8.408280778E−09 | −9.933576982E−09 | 1.024137839E−10 |
| $c_{22-24}$ | 8.699296183E−11 | 3.577829179E−10 | −2.664015377E−10 |
| $c_{25-27}$ | −1.672652883E−10 | 1.189377902E−10 | 5.791978628E−11 |

Surface $2_h$:

| | | | |
|---|---|---|---|
| $K_x$ = | 0.000000000E+00 | $K_y$ = | 0.000000000E+00 |
| $1/\rho_x$ = | −100.942861 | $1/\rho_y$ = | −98.378083 |
| $c_{1-3}$ | −9.161670241E−03 | −8.788093654E−02 | 1.408964249E−03 |
| $c_{4-6}$ | 2.635200694E−04 | −8.975033724E−04 | −7.969861973E−06 |
| $c_{7-9}$ | 1.533812116E−05 | 6.184418241E−05 | −6.612799354E−06 |
| $c_{10-12}$ | 1.204845982E−06 | −1.699698381E−07 | 7.087299744E−07 |
| $c_{13-15}$ | −4.163252796E−07 | 1.166367085E−07 | −1.912225085E−08 |
| $c_{16-18}$ | 1.977850174E−09 | −8.419477563E−09 | −1.643242739E−08 |
| $c_{19-21}$ | −1.525863528E−08 | −9.707951413E−09 | 2.251616020E−10 |
| $c_{22-24}$ | 1.032924328E−10 | 2.605738887E−10 | 6.669331923E−11 |
| $c_{25-27}$ | −7.352489548E−13 | 9.986952257E−12 | 1.275821826E−10 |

Surface $3_h$:

| | | | |
|---|---|---|---|
| $K_x$ = | 0.000000000E+00 | $K_y$ = | 0.000000000E+00 |
| $1/\rho_x$ = | −626.781667 | $1/\rho_y$ = | −553.072593 |
| c1-3 | 9.589635860E−04 | −2.793454122E−02 | 2.543402884E−03 |
| $c_{4-6}$ | 5.603206875E−04 | 5.231844352E−03 | −749139943E−05 |

-continued

| | | | |
|---|---|---|---|
| $c_{7-9}$ | −1.274965695E−04 | −1.490895306E−04 | −8.223942953E−05 |
| $c_{10-12}$ | −7.767776527E−08 | 8.031767435E−07 | 2.666657937E−06 |
| $c_{13-15}$ | 1.243910582E−07 | 4.703770967E−07 | 2.285599114E−08 |
| $c_{16-18}$ | 2.782537511E−08 | 1.728369546E−08 | −4.077973829E−08 |
| $c_{19-21}$ | 2.806803694E−08 | −1.355578289E−08 | −3.765213129E−10 |
| $c_{22-24}$ | −1.470696533E−10 | −1.629135913E−09 | 1.752264004E−10 |
| $c_{25-27}$ | 3.089575802E−10 | 1.268262112E−09 | −3.185215617E−10 |

Figure 4A:
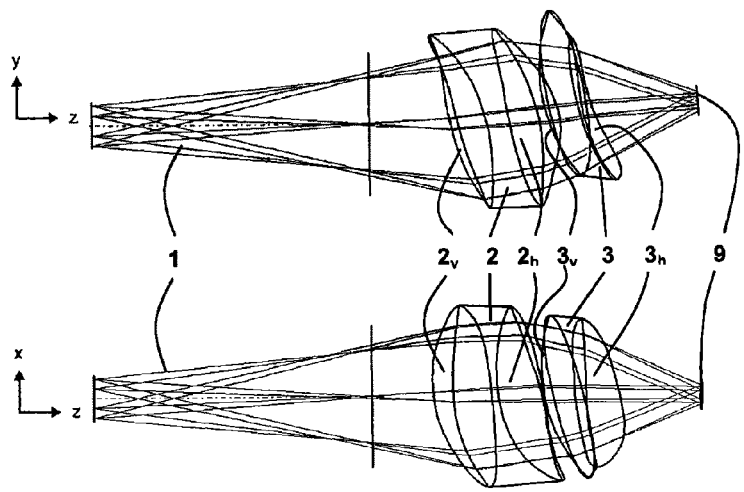
FIG. 4a depicts the illumination beam path of a third imaging optics system, according to the invention, with two refractive optical elements, the system surfaces of which are designed in the form of three free-form surfaces, and a sphere.

Thereto, FIG. 4a shows the (idealized) illumination beam path of the third imaging optics, according to the invention, with two refractive optical elements, the system surfaces of which are designed in the form of three free-form surfaces, and a sphere. The use of spherical and, particularly, a rotationally symmetrical, spherical system surface simplifies the manufacture of the refractive optical elements significantly.

Hereby, the illumination beams 1 in the form of an annular illumination are also focused in the eye pupil plane 9, starting from the (not depicted) illumination source via two refractive optical elements 2 and 3. Single reflections (not depicted) of the illumination beams 1, which occur at the optical system surfaces $2_v$ and $2_h$ as well as $3_v$ and $3_h$, are also to be blocked out for the observation. For said purpose, the system surfaces of the two refractive, approximately wedge-shaped optical elements 2 and 3, tilted at a random azimuth angle of at least 5° and/or positioned off-center in the beam path, are designed as free-form surfaces, with the exception of the anterior system surface $3_v$ of the second refractive optical element 3, which is designed as an asphere.

Figure 4B:
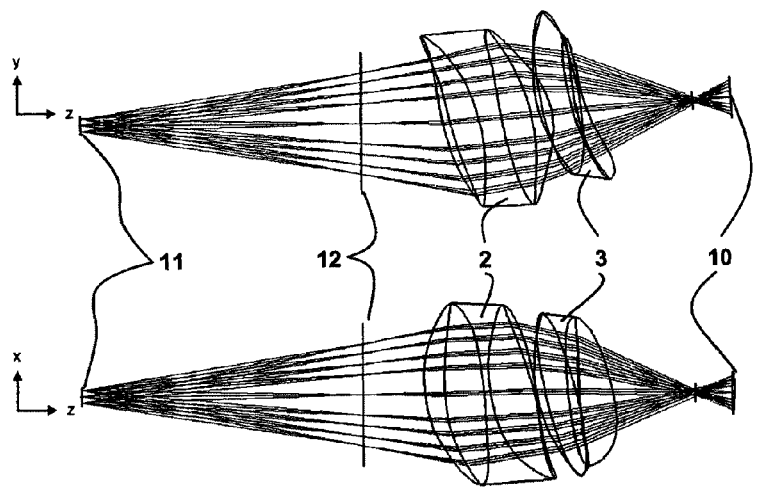
FIG. 4b depicts the observation beam path of a third imaging optics system, according to the invention, with two refractive optical elements, the system surfaces of which are designed in the form of three free-form surfaces, and a sphere.

FIG. 4b shows the respective observation beam path of the third imaging optics, according to the invention, with two refractive optical elements, the system surfaces of which are designed in the form of three free-form surfaces, and a sphere, as well as an eye idealized through a substitute focal length.

The image of the retina 10 is mapped in the aperture diaphragm 11 via the two refractive optical elements 2 and 3, whereby an intermediate image of the retina is produced in the plane 12. Through the optical system surfaces $2_v$ and $2_h$ as well as $3_v$ and $3_h$, designed in accordance with the invention, occurring single reflections (not depicted) of the illumination beams are blocked out for the observation, therefore not impinging on the aperture diaphragm 11.

Contrary to the solutions in prior art and the previously described solutions, the distortion values achieved with this solution are less than 1.2% for an angle of field of up to 30° and less than 1.5% for the entire angle of field of 48°.

Figure 4C:
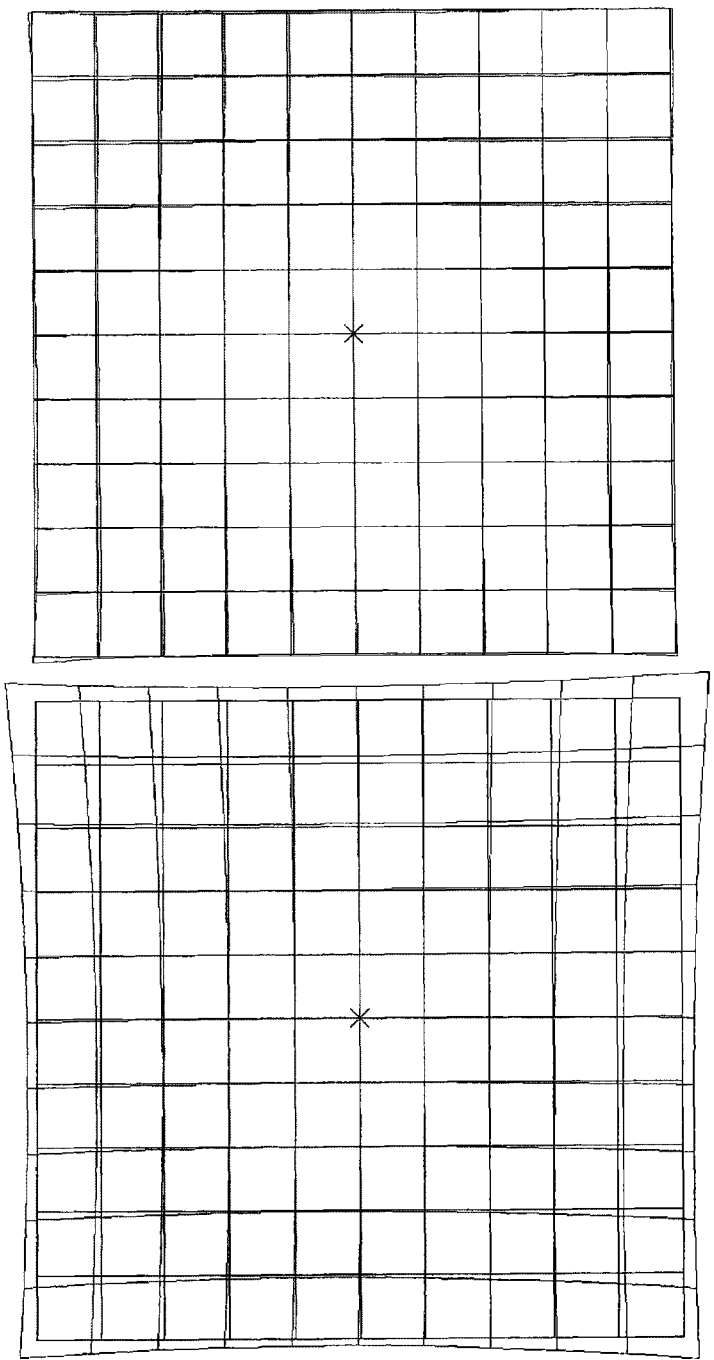
FIG. 4c depicts the thereby occurring distortion grid related to FIGS. 4b and 4c of the imaging optics on the retina juxtaposed to imaging optics known from prior art.

Thereto, FIG. 4c shows for this solution the occurring distortion grid of the imaging optics on the retina juxtaposed to the distortion grid of imaging optics known from prior art, according to DE 103 16 416 A1.

Figure 4D:
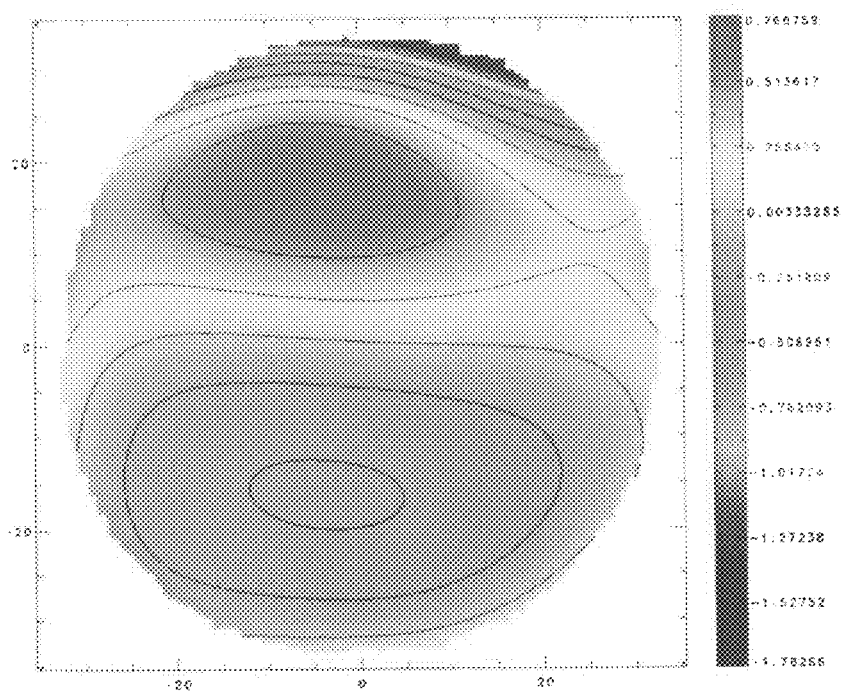
FIG. 4d is a depiction of the sagittal height deviation of the free-form surface on the anterior system surface of the first refractive optical element to a fitted rotationally symmetrical asphere.

In the previously described embodiment examples two and three, three of the four optical system surfaces were designed as free-form surfaces, with deviation in the sagittal height to the best adjusted rotationally symmetrical aspheres from +/−0.4 mm to +/−1.6 mm. Thereto, FIG. 4d shows the depiction of the sagittal height deviation of the free-form surface on the anterior system surface 2, of the first refractive optical element 2 with regard to a fitted rotationally symmetrical asphere. These tremendous deviations from the rotational symmetry illustrate the necessity of free-form surfaces for the non-reflective imaging optics, according to the invention.

The herein suggested and described third embodiment example is characterized by the non-reflection in the area of interest, very little distortion, a wide open working distance, and only two refractive optical elements, which are comparatively small and manufactured cost-effectively, whereby one optical functional surface is designed as a sphere which has a positive effect on the manufacture of said element.

In a further advantageous embodiment, the non-reflective imaging optics consist of three refractive optical elements which are designed approximately wedge-shaped and tilted at a random azimuth angle of at least 5° and/or are positioned off-center in the beam path in order to block out the single reflections of the illumination, occurring at the optical system surfaces, for the observation.

For the control of the distortion and the symmetrization of monochromatic image defects, which otherwise, due to the tilt of the system surfaces and elements, the wedge shape of the lenses and the possible approximate toric effect of system surfaces, turn out very unsymmetrical, it suffices for this embodiment variation that at least one of the optical system surfaces of the three refractive optical elements, approximately wedge-shaped and tilted in the beam path, is designed as a free-form surface. Thereby, the remaining optical system surfaces can exhibit an aspherical, toric, or even a spherical form.

Through the use of spherical system surfaces instead of rotationally symmetrical aspheres, the manufacture of the refractive optical elements can be significantly simplified. Embodiments with exactly three refractive optical elements are advantageous since the application of free-form surfaces allows for the realization of even more compact and simpler designs than those solutions known from prior art. Compared to embodiments with only two refractive optical elements, even better corrections, particularly of chromatic aberrations, are possible.

In a last, particularly advantageous embodiment, the refractive optical elements, regardless of the form of their system surfaces, are fabricated through injection molding with a polymer material.

This would simplify the manufacture of the overall assembly and decrease the demands on mounting and alignment due to the significant weight reduction.

Advantageously, so-called EA-DOEs (efficiency achromatized diffractive optical elements) can hereby be utilized for the correction of occurring longitudinal chromatic aberrations and transverse chromatic aberrations.

The advantageous technical effects achieved with the design, according to the invention, are:

The prevention of stray light from single reflections at optical boundary layers through optical elements utilized jointly by the illumination system and the observation system;

Guarantee of compact and light components;

Avoidance of elaborate mechanics and software for scanning systems; and

Avoidance of elaborate cost-intensive manufacture and alignment of mirror elements with surface shapes which break the rotational symmetry.

Above all, the use of free-form surfaces enables the control of the distortion and symmetrization of the monochromatic image defects, which otherwise, due to the tilt of the system surfaces and elements, the wedge shape of the lenses and the possible approximate toric effect of system surfaces, turn out very unsymmetrical.

Through the exclusive utilization of refractive optical elements, the tolerance sensitivity with regard to surface demands and position is significantly lower. Furthermore, the frame size of the elements is drastically reduced. As a result, a system can be fabricated and aligned with less effort when compared to a solution with reflective elements.

The use of approximately/basically toric surfaces has proven to be beneficial. As a result, the form of the reflections is affected in such a way that a small tilt suffices for blocking out the reflection. This leads to a symmetry break with unsymmetrical higher-order aberrations which are both less strong.

The invention claimed is:

1. Non-reflective imaging optics for optical devices, in general and in ophthalmology,
comprising at least two refractive optical elements including a first refractive optical element and a second refractive optical element, which are utilized for illumination as well as observation, wherein the at least two refractive optical elements are approximately wedge-shaped and are tilted at a random azimuth angle of at least 5° and/or are positioned off-center in the beam path to completely block out single reflections of the illumination, occurring at the optical system surfaces, for the observation;
wherein at least two optical system surfaces of the at least two refractive optical elements, are designed as free-form surfaces, while remaining optical system surfaces of the at least two refractive optical elements are aspherical, toric or spherical in form.

2. Non-reflective imaging optics, according to claim 1, wherein the optical system surfaces, designed as free-form surfaces, of the at least two refractive optical elements, which are designed approximately wedge-shaped and tilted in the beam path, are toric in form.

3. Non-reflective imaging optics, according to claim 1, wherein exactly two refractive optical elements are designed approximately wedge-shaped and are tilted at a random azimuth angle of at least 5° and/or are positioned off-center in the beam path to completely block out single reflections of the illumination, occurring at the optical system surfaces, for the observation.

4. Non-reflective imaging optics, according to claim 1, wherein anterior system surfaces of both refractive optical elements comprise free-form surfaces, a posterior system surface of the first refractive optical element is designed as torus, and a posterior system surface of the second refractive optical element is designed as sphere, and the overall design of the Non-reflective imaging optics is described as follows:

| Surface | Radius [mm] | Thickness [mm] | Glass | Comment |
|---|---|---|---|---|
| SA = BQ | 0.000000 | 127.023559 | | |
| ZB | 0.000000 | 33.434954 | | |
| $2_v$ | 460.241355 | 40.000000 | N-LAK8 | XY polynomial |
| $2_h$ | −112.724233 | 3.416369 | | Torus |
| $3_v$ | 67.330573 | 21.208847 | N-LAK8 | Sphere |
| $3_h$ | −553.072593 | 49.259906 | | XY polynomial |
| P = IA | 0.000000 | 17.000000Y | Ideal lens | f = 17 mm |
| R | 0.000000 | | | |

Position of the surfaces:
Translation of the coordinate systems:

| Surface | X [mm] | Y [mm] | Z [mm] |
|---|---|---|---|
| $2_v$ | −0.015804 | −0.009449 | 0.000000 |
| $2_h$ | −0.176313 | 4.129852 | 0.000000 |
| $3_v$ | −1.160058 | 9.969841 | 0.000000 |
| $3_h$ | 0.397186 | 4.114025 | 0.000000 |
| P = IA | 0.194216 | 2.831227 | 0.000000 |

Rotation of the coordinate systems with regard to eye pupil (in air):

| Surface | Alpha [degree] | Beta [degree] | Gamma [degree] |
|---|---|---|---|
| $2_v$ | −9.715970 | −0.842779 | 0.000000 |
| $2_h$ | −14.376718 | 16.307588 | 0.000000 |
| $3_v$ | −9.946335 | 15.458494 | 0.000000 |
| $3_h$ | −11.913235 | 2.391050 | 0.000000 |
| P = IA | 1.482621 | −0.261571 | −0.138182 |

Description of the surface shapes of surfaces $2_v$, $2_h$, $3_h$:

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

Surface $2_v$:

| $K_x =$ | 0.000000000E+00 | $K_y =$ | 0.000000000E+00 |
|---|---|---|---|
| $1/\rho_x =$ | 262.029626 | $1/\rho_y =$ | 460.241355 |
| $c_{1\text{-}3}$ | −8.16682913E−02 | 1.30744652E−02 | 3.41935416E−03 |
| $c_{4\text{-}6}$ | −7.06926443E−04 | 2.79954523E−03 | −7.24668714E−05 |
| $c_{7\text{-}9}$ | −7.13866226E−05 | −8.22329726E−05 | −7.79315372E−05 |

-continued

|  |  |  |  |
|---|---|---|---|
| $c_{10-12}$ | −3.21596886E−07 | 1.76630879E−07 | −5.03015616E−07 |
| $c_{13-15}$ | −2.78639559E−07 | −1.02664121E−06 | 8.17043798E−09 |
| $c_{16-18}$ | 1.47741005E−08 | 2.45319524E−08 | −6.39279788E−09 |
| $c_{19-21}$ | 7.16686190E−09 | −2.93771547E−09 | 2.40054911E−11 |
| $c_{22-24}$ | 3.80865136E−12 | 3.12139213E−10 | −2.66011419E−10 |
| $c_{25-27}$ | −2.10800584E−10 | 8.11033757E−11 | 1.06969528E−11 |

Surface $2_h$:

| | | | |
|---|---|---|---|
| $K_x =$ | 0.000000000E+00 | $K_y =$ | 0.000000000E+00 |
| $1/\rho_x =$ | −192.389983 | $1/\rho_y =$ | −112.724233 |
| $c_{1-27}$ | 0.000000000E−00 | | |

Surface $3_h$:

| | | | |
|---|---|---|---|
| $K_x =$ | 0.000000000E+00 | $K_y =$ | 0.000000000E+00 |
| $1/\rho_x =$ | −626.781667 | $1/\rho_y =$ | −553.072593 |
| $c_{1-3}$ | 1.46571567E−02 | −4.19559905E−02 | 2.47038454E−03 |
| $c_{4-6}$ | 1.30391601E−03 | 4.05033404E−03 | −1.10654287E−04 |
| $c_{7-9}$ | −1.18192140E−04 | −1.08606641E−04 | −1.01909142E−04 |
| $c_{10-12}$ | −9.70012347E−07 | 5.68458154E−07 | 3.06807937E−06 |
| $c_{13-15}$ | −1.85585147E−07 | 5.49978310E−07 | 1.31161920E−08 |
| $c_{16-18}$ | 2.50938306E−08 | 2.12181386E−08 | −4.80230112E−08 |
| $c_{19-21}$ | −4.51844849E−09 | −1.37209572E−08 | −2.41037488E−10 |
| $c_{22-24}$ | −9.94991837E−11 | −1.48481266E−09 | 3.35571849E−10 |
| $c_{25-27}$ | 5.06355656E−10 | 7.62147783E−10 | 3.68207235E−10. |

5. Non-reflective imaging optics, according to claim 1, wherein an anterior and a posterior system surface of the first refractive optical element, and the posterior system surface of the second refractive optical element comprise a free-form surface, and an anterior system surface of the second refractive optical element comprises an asphere and the overall design of Non-reflective imaging optics is described as follows:

| Surface | Radius [mm] | Thickness [mm] | Glass | Comment |
|---|---|---|---|---|
| SA = BQ | 0.000000 | 112.723657 | | |
| ZB | 0.000000 | 26.315884 | | |
| $2_v$ | 460.241355 | 40.000000 | N-LAK8 | XY polynomial |
| $2_h$ | −98.378083 | 2.432516 | | XY polynomial |
| $3_v$ | 69.369038 | 18.428907 | N-LAK8 | Asphere |
| $3_h$ | −553.072593 | 45.324601 | | XY polynomial |
| P = IA | 0.000000 | 17.000000Y | Ideal lens | f = 17 mm |
| R | 0.000000 | | | |

Position of the surfaces:
Translation of the coordinate systems:

| Surface | X [mm] | Y [mm] | Z [mm] |
|---|---|---|---|
| $2_v$ | −0.008249 | −0.004878 | 0.000000 |
| $2_h$ | −3.632256 | 4.940808 | 0.000000 |
| $3_v$ | −7.513007 | 12.906752 | 0.000000 |
| $3_h$ | −6.767967 | 10.354774 | 0.000000 |
| P = IA | −15.095604 | 20.046330 | 0.000000 |

Rotation of the coordinate systems with regard to eye pupil (in air):

| Surface | Alpha [degree] | Beta [degree] | Gamma [degree] |
|---|---|---|---|
| $2_v$ | −16.627633 | −12.552204 | 0.000000 |
| $2_h$ | −2.975360 | 9.652402 | 0.000000 |
| $3_v$ | −18.533878 | 9.595629 | 0.000000 |
| $3_h$ | −17.902422 | 1.472894 | 0.000000 |
| P = IA | −12.055657 | −10.186383 | −1.343352 |

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

Description of the surface shapes of surfaces $2_v$, $2_h$, $3_h$:
Surface $2_v$:

| | | | |
|---|---|---|---|
| $K_x =$ | 0.000000000E+00 | $K_y =$ | 0.000000000E+00 |
| $1/\rho_x =$ | 262.029626 | $1/\rho_y =$ | 460.241355 |
| $c_{1-3}$ | −1.076219235E−02 | −1.939046941E−03 | 1.997905625E−03 |

-continued

|  | | | |
|---|---|---|---|
| $c_{4-6}$ | 1.746907059E−03 | 2.461118134E−03 | −6.571983437E−05 |
| $c_{7-9}$ | −9.883077652E−06 | −5.445029935E−05 | −1.632332880E−05 |
| $c_{10-12}$ | −3.984223970E−07 | 6.025247976E−07 | −3.447675743E−07 |
| $c_{13-15}$ | 6.588778570E−08 | −9.912377449E−07 | 6.020462360E−09 |
| $c_{16-18}$ | −1.953270172E−10 | 7.786357428E−09 | −1.948376196E−09 |
| $c_{19-21}$ | 7.040827309E−09 | −8.579730212E−09 | 1.890823354E−10 |
| $c_{22-24}$ | 1.545069767E−11 | −3.939617920E−11 | −1.872836301E−10 |
| $c_{25-27}$ | −1.433811680E−10 | −3.180424756E−10 | 5.075901345E−11 |

Surface $2_h$:

|  | | | |
|---|---|---|---|
| $K_x =$ | 0.000000000E+00 | $K_y =$ | 0.000000000E+00 |
| $1/\rho_x =$ | −100.942861 | $1/\rho_y =$ | −98.378083 |
| $c_{1-3}$ | 5.282970718E−03 | −2.390734163E−02 | 9.280180593E−04 |
| $c_{4-6}$ | 7.885552729E−04 | −1.715965007E−03 | 2.046197629E−05 |
| $c_{7-9}$ | 1.927024556E−05 | 8.531615103E−05 | −1.605061381E−05 |
| $c_{10-12}$ | 5.617458102E−07 | 3.689124959E−07 | 7.443694101E−07 |
| $c_{13-15}$ | −5.994160512E−07 | 2.282951119E−07 | −5.812076272E−09 |
| $c_{16-18}$ | −1.723649589E−09 | −8.769239055E−09 | −9.773820261E−10 |
| $c_{19-21}$ | −4.698271820E−09 | −1.704652063E−08 | 1.317751719E−10 |
| $c_{22-24}$ | 2.089880410E−10 | 3.761425386E−10 | 1.878879381E−10 |
| $c_{25-27}$ | −7.245340147E−11 | −9.975912395E−11 | −9.207989014E−11 |

Surface $3_h$:

|  | | | |
|---|---|---|---|
| $K_x =$ | 0.000000000E+00 | $K_y =$ | 0.000000000E+00 |
| $1/\rho_x =$ | −626.781667 | $1/\rho_y =$ | −553.072593 |
| $c_{1-3}$ | 2.487303401E−02 | −6.337149712E−02 | 5.842772050E−04 |
| $c_{4-6}$ | 3.650951912E−04 | 3.800070084E−03 | −6.340939346E−05 |
| $c_{7-9}$ | −4.948991848E−05 | −1.560159975E−04 | −2.586127402E−05 |
| $c_{10-12}$ | 9.681634924E−07 | 9.072631039E−07 | 1.675755763E−06 |
| $c_{13-15}$ | 9.789720502E−07 | 5.079850594E−07 | 9.057671419E−09 |
| $c_{16-18}$ | −5.038663621E−09 | −6.726531096E−10 | −2.375679687E−08 |
| $c_{19-21}$ | −3.868956663E−09 | −1.420798036 − 08 | −4.135849189E−10 |
| $c_{22-24}$ | −7.758610476E−11 | −1.701714743E−09 | −1.760333486E−11 |
| $c_{25-27}$ | −5.742161539E−10 | −1.914559861E−11 | −3.980153064E−10 |

Description of the surface shape of surface $3_v$:

$$z = \frac{\rho h^2}{1 + \sqrt{1 - (1+\kappa)\rho^2 h^2}} + \sum_{k=1} c_k h^{2k+2}$$

| | | | |
|---|---|---|---|
| K = | 8.835330521E−02 | | |
| $1/\rho =$ | 69.369038 | | |
| c1-3 | 0.000000000E−00 | 0.000000000E−00 | 0.000000000E−00. |

6. Non-reflective imaging optics, according to claim 1, wherein an anterior and a posterior system surface of the first refractive optical element, and a posterior system surface of the second refractive optical element comprise free-form surfaces, and an anterior system surface of the second refractive optical element is designed as a sphere, and an overall design of the Non-reflective imaging optics is described as follows:

| Surface | Radius [mm] | Thickness [mm] | Glass | Comment |
|---|---|---|---|---|
| SA = BQ | 0.000000 | 123.394223 | | |
| ZB | 0.000000 | 36.178305 | | |
| $2_v$ | 460.241355 | 39.210908 | N-LAK8 | XY polynomial |
| $2_h$ | −98.378083 | 2.041868 | | XY polynomial |
| $3_v$ | 69.665916 | 17.941242 | N-LAK8 | |
| $3_h$ | −553.072593 | 50.945958 | | XY polynomial |
| P = IA | 0.000000 | 17.000000Y | Ideal lens | f′ = 17 mm |
| R | 0.000000 | | | |

Position of the surfaces:
Translation of the coordinate systems:

| Surface | X [mm] | Y [mm] | Z [mm] |
|---|---|---|---|
| $2_v$ | −0.011617 | −0.016130 | 0.000000 |
| $2_h$ | 0.974295 | 3.470584 | 0.000000 |
| $3_v$ | −3.363366 | 10.952433 | 0.000000 |
| $3_h$ | 0.658348 | 5.474388 | 0.000000 |
| P = IA | −0.182751 | 9.037957 | 0.000000 |

-continued

Rotation of the coordinate systems with regard to eye pupil (in air):

| Surface | Alpha [degree] | Beta [degree] | Gamma [degree] |
|---|---|---|---|

$$z = \frac{\rho_x x^2 + \rho_y y^2}{1 + \sqrt{1 - (1+\kappa_x)\rho_x^2 x^2 - (1+\kappa_y)\rho_y^2 y^2}} + c_1 \cdot x + c_2 \cdot y + c_3 \cdot x^2 + c_4 \cdot x \cdot y +$$

$$c_5 \cdot y^2 + c_6 \cdot x^3 + c_7 \cdot x^2 \cdot y + c_8 \cdot x \cdot y^2 + c_9 \cdot y^3 + c_{10} \cdot x^4 + c_{11} \cdot x^3 \cdot y + \ldots$$

| Surface | Alpha [degree] | Beta [degree] | Gamma [degree] |
|---|---|---|---|
| $2_v$ | −11.950087 | −1.103246 | 0.000000 |
| $2_h$ | −7.561127 | 12.292050 | 0.000000 |
| $3_v$ | −10.640443 | 13.236519 | 0.000000 |
| $3_h$ | −9.340704 | 1.838853 | 0.000000 |
| P = IA | −3.992984 | −0.936974 | 0.033760 |

Description of the surface shapes of surfaces $2_v$, $2_h$, $3_h$:
Surface $2_v$:

| | | | |
|---|---|---|---|
| $K_x =$ | 0.000000000E+00 | $K_y =$ | 0.000000000E+00 |
| $1/\rho_x =$ | 262.029626 | $1/\rho_y =$ | 460.241355 |
| $c_{1-3}$ | −7.816294472E−02 | −6.769775549E−04 | 3.512000519E−03 |
| $c_{4-6}$ | −1.933397623E−04 | 3.323904852E−03 | −7.073432239E−05 |
| $c_{7-9}$ | −5.175690025E−05 | −4.246655458E−05 | −5.977805266E−05 |
| $c_{10-12}$ | 1.661105408E−07 | 2.387423681E−07 | −2.140049981E−07 |
| $c_{13-15}$ | −2.624390743E−07 | −1.155402838E−06 | 5.256645482E−09 |
| $c_{16-18}$ | 1.507180023E−08 | 2.590824277E−08 | −9.019395714E−09 |
| $c_{19-21}$ | 8.408280778E−09 | −9.933576982E−09 | 1.024137839E−10 |
| $c_{22-24}$ | 8.699296183E−11 | 3.577829179E−10 | −2.664015377E−10 |
| $c_{25-27}$ | −1.672652883E−10 | 1.189377902E−10 | 5.791978628E−11 |

Surface $2_h$:

| | | | |
|---|---|---|---|
| $K_x =$ | 0.000000000E+00 | $K_y =$ | 0.000000000E+00 |
| $1/\rho_x =$ | −100.942861 | $1/\rho_y =$ | −98.378083 |
| $c_{1-3}$ | −9.161670241E−03 | −8.788093654E−02 | 1.408964249E−03 |
| $c_{4-6}$ | 2.635200694E−04 | −8.975033724E−04 | −7.969861973E−06 |
| $c_{7-9}$ | 1.533812116E−05 | 6.184418241E−05 | −6.612799354E−06 |
| $c_{10-12}$ | 1.204845982E−06 | −1.699698381E−07 | 7.087299744E−07 |
| $c_{13-15}$ | −4.163252796E−07 | 1.166367085E−07 | −1.912225085E−08 |
| $c_{16-18}$ | 1.977850174E−09 | −8.419477563E−09 | −1.643242739E−08 |
| $c_{19-21}$ | −1.525863528E−08 | −9.707951413E−09 | 2.251616020E−10 |
| $c_{22-24}$ | 1.032924328E−10 | 2.605738887E−10 | 6.669331923E−11 |
| $c_{25-27}$ | −7.352489548E−13 | 9.986952257E−12 | 1.275821826E−10 |

Surface $3_h$:

| | | | |
|---|---|---|---|
| $K_x =$ | 0.000000000E+00 | $K_y =$ | 0.000000000E+00 |
| $1/\rho_x =$ | −626.781667 | $1/\rho_y =$ | −553.072593 |
| $c_{1-3}$ | 9.589635860−04 | −2.793454122E−02 | 2.543402884E−03 |
| $c_{4-6}$ | 5.603206875E−04 | 5.231844352E−03 | −749139943E−05 |
| $c_{7-9}$ | −1.274965695E−04 | −1.490895306E−04 | −8.223942953E−05 |
| $c_{10-12}$ | −7.767776527E−08 | 8.031767435E−07 | 2.666657937E−06 |
| $c_{13-15}$ | 1.243910582E−07 | 4.703770967E−07 | 2.285599114E−08 |
| $c_{16-18}$ | 2.782537511E−08 | 1.728369546E−08 | −4.077973829E−08 |
| $c_{19-21}$ | 2.806803694E−08 | −1.355578289E−08 | −3.765213129E−10 |
| $c_{22-24}$ | −1.470696533E−10 | −1.629135913E−09 | 1.752264004E−10 |
| $c_{25-27}$ | 3.089575802E−10 | 1.268262112E−09 | −3.185215617E−10. |

7. Non-reflective imaging optics, according to claim 1, wherein three refractive optical elements are utilized, each of which is designed approximately wedge-shaped and tilted at a random azimuth angle of at least 5° and/or are positioned off-center in the beam path in order to block out single reflections of the illumination, occurring at the optical system surfaces, for the observation.

8. Non-reflective imaging optics, according to claim 7, characterized in that at least one of the optical system surfaces of the three refractive optical elements, designed approximately wedge-shaped and tilted in the beam path, is designed as a free-form surface, while the remaining optical system surfaces of the three refractive optical elements, designed approximately wedge-shaped and tilted in the beam path, are aspherical, toric, or spherical in form.

* * * * *